(12) United States Patent
Costello (10) Patent No.: US 10,238,515 B2
(45) Date of Patent: *Mar. 26, 2019

(54) CONTROL SYSTEM FOR A STENT DELIVERY SYSTEM

(71) Applicant: Cook Medical Technologies LLC, Bloomington, IN (US)

(72) Inventor: Kieran Costello, Clare (IE)

(73) Assignee: Cook Medical Technologies LLC, Bloomington, IN (US)

( * ) Notice: Subject to any disclaimer, the term of this patent is extended or adjusted under 35 U.S.C. 154(b) by 220 days.

This patent is subject to a terminal disclaimer.

(21) Appl. No.: 15/090,828

(22) Filed: Apr. 5, 2016

(65) Prior Publication Data

US 2016/0213502 A1 Jul. 28, 2016

Related U.S. Application Data

(63) Continuation of application No. 13/495,234, filed on Jun. 13, 2012, now Pat. No. 9,333,103.

(Continued)

(51) Int. Cl.
*A61F 2/962* (2013.01)
*A61F 2/844* (2013.01)
(Continued)

(52) U.S. Cl.
CPC .............. *A61F 2/962* (2013.01); *A61F 2/844* (2013.01); *A61F 2/95* (2013.01);
(Continued)

(58) Field of Classification Search
CPC .................................... A61F 2/95–2/97; A61F 2002/9505–2002/9665
See application file for complete search history.

(56) References Cited

U.S. PATENT DOCUMENTS

| 4,601,301 A | 7/1986 | Hermanson |
| 6,168,616 B1 | 1/2001 | Brown, III |

(Continued)

FOREIGN PATENT DOCUMENTS

| JP | 2002 177318 A | 6/2002 |
| WO | WO 2002/066094 A2 | 8/2002 |

(Continued)

OTHER PUBLICATIONS

International Search Report dated Oct. 26, 2012 for International Application No. PCT/US2012/042173.

(Continued)

*Primary Examiner* — Darwin P Erezo
*Assistant Examiner* — Jonathan A Hollm
(74) *Attorney, Agent, or Firm* — Brinks Gilson & Lione (57) ABSTRACT

A control system for controlling movement of a medical device delivery system, a stent delivery system and a method for controlling movement of a medical device delivery system are provided. The control system includes a first extendable arm comprising a plurality of first struts interconnected at intermediate points and end points of the first struts. The first arm is movable between a first position and a second position and the first arm is operably connected to one of the first shaft and the second shaft. The control system also includes a first actuator operably connected to the first arm and the first actuator is operable to move the first arm from the first position to the second position. Movement of the first arm moves the first shaft relative to the second shaft to change the position of the second shaft relative to the first shaft.

17 Claims, 6 Drawing Sheets

Related U.S. Application Data (60) Provisional application No. 61/499,261, filed on Jun. 21, 2011.

(51) Int. Cl.
*A61F 2/95* (2013.01)
*A61F 2/966* (2013.01)

(52) U.S. Cl.
CPC .............. *A61F 2002/9511* (2013.01); *A61F 2002/9517* (2013.01); *A61F 2002/9534* (2013.01); *A61F 2002/9665* (2013.01); *A61F 2220/0091* (2013.01); *A61F 2230/0058* (2013.01)

(56) References Cited

U.S. PATENT DOCUMENTS

| | | |
|---|---|---|
| 6,855,156 B2 | 2/2005 | Etter et al. |
| 7,052,511 B2* | 5/2006 | Weldon ............... A61F 2/95 606/194 |
| 7,255,314 B2 | 8/2007 | Hanson et al. |
| 2002/0111666 A1* | 8/2002 | Hart ..................... A61F 2/95 623/1.11 |
| 2003/0225445 A1 | 12/2003 | Derus et al. |
| 2006/0111771 A1 | 5/2006 | Ton et al. |
| 2006/0173524 A1 | 8/2006 | Salahieh et al. |
| 2011/0190865 A1 | 8/2011 | McHugo |

FOREIGN PATENT DOCUMENTS

| | | |
|---|---|---|
| WO | WO 2005/115254 A2 | 12/2005 |
| WO | WO 2009/026272 A1 | 2/2009 |

OTHER PUBLICATIONS

Written Opinion dated Oct. 26, 2012 for International Application No. PCT/US2012/042173.

Communication pursuant to Article 94(3) EPC dated Aug. 25, 2017 for European Application No. 12 731 798.0-1651.

\* cited by examiner

CONTROL SYSTEM FOR A STENT DELIVERY SYSTEM

RELATED APPLICATIONS

This application is a continuation of U.S. application Ser. No. 13/495,234, filed Jun. 13, 2012, which claims the benefit of U.S. Provisional Application No. 61/499,261, filed Jun. 21, 2011, which are incorporated by reference herein in their entirety.

TECHNICAL FIELD

This invention relates to a medical device and, in particular to a control system for a device for delivering and deploying a stent and a method of controlling the stent delivery system.

BACKGROUND

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. radially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catheters and hysteresis in the movement of the stent. The sheathed stent delivery device also requires more space within an endoscope compared to a sheathless device and also adds additional expense to the delivery system.

A longitudinally tensioned stent delivery system has been developed to avoid some of the drawbacks that can occur with a sheathed delivery device described above. The longitudinally tensioned stent delivery system includes an inner and an outer shaft coaxially positioned and longitudinally moveable in relation to each other to expand and constrain a stent positioned on the inner and outer shafts that can increase the control, accuracy and ease of placement of a stent during deployment of the stent within a patient. A control mechanism for controlling the movement of the inner and outer shafts relative to each other is needed to control the longitudinally tensioned stent delivery system to provide the ability to deliver the stent to the desired position and to be able to reconstrain, recapture, reposition and/or remove the stent after expansion of the stent.

SUMMARY OF THE INVENTION

Accordingly, it is an object of the present invention to provide a device and a method having features that resolve or improve on one or more of the above-described drawbacks.

The foregoing object is obtained in one aspect of the present invention by providing a control system for controlling movement of a medical device delivery system having a first shaft and a second shaft, the first shaft is movable relative to the second shaft. The control system includes a first extendable arm comprising a plurality of first struts interconnected at intermediate points and end points of the first struts. The first arm is movable between a first position and a second position and the first arm is operably connected to one of the first shaft and the second shaft. The control system also includes a first actuator operably connected to the first arm and the first actuator is operable to move the first arm from the first position to the second position. Movement of the first arm moves the first shaft relative to the second shaft to change the position of the second shaft relative to the first shaft.

In another aspect of the present invention, a stent delivery system is provided. The stent delivery system includes a first shaft and a second shaft, the second shaft movable relative to the first shaft and coaxially extending with the first shaft. The delivery system also includes a stent operably connected to the first shaft and the second shaft and a control system. The control system includes a first extendable arm including a plurality of first struts interconnected at intermediate points and end points of the first struts wherein the first arm is movable between a first position and a second position. The first arm is operably connected to one of the first shaft and the second shaft. The control system also includes a first actuator operably connected to the first arm wherein the first actuator is operable to move the first arm from the first position to the second position. Movement of the first arm moves the first shaft relative to the second shaft to change the position of the stent relative to the first shaft.

In another aspect of the present invention, a method for implanting a stent using a medical device delivery system is provided. The method includes providing a control system. The control system includes a first extendable arm including a plurality of first struts interconnected at intermediate points and end points of the first struts wherein the first arm is movable between a first position and a second position. The first arm is operably connected to one of the first shaft and the second shaft. The control system also includes a first actuator operably connected to the first arm wherein the first actuator is operable to move the first arm from the first position to the second position. The method further includes activating the first actuator, moving the first arm in response to the activation of the first actuator, and changing the position of the first shaft relative to the second shaft.

DETAILED DESCRIPTION OF THE EMBODIMENTS

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

Figure 1:
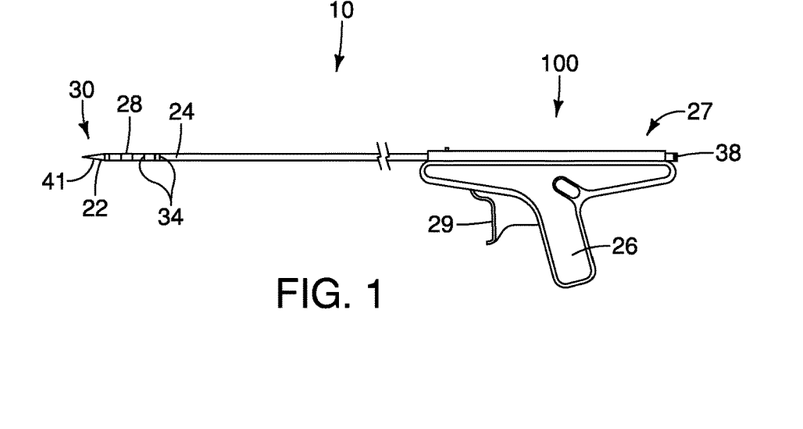
FIG. 1 is a side view of a stent delivery system.

FIG. 1 illustrates an exemplary stent delivery system 10 that may be provided with a control system 100 according to an embodiment of the present invention. The delivery system 10 may be provided as an over-the-wire configuration or a rapid exchange configuration. The stent delivery system 10 includes an inner shaft 22, an outer shaft 24 and a handle 26 at a proximal portion 27 of the system 10. The handle 26 may also include a trigger 29 for actuating the control system 100. The stent delivery system 10 also includes a stent 28 at a distal portion 30 of the delivery system 10. One or more radiopaque markers 34 may be included on the delivery system 10 to indicate the position of the stent 28. The stent delivery system 10 may also include a guide wire (not shown) extendable through a port 38 of the inner shaft 22 through a distal tip 41 at the distal portion 30 of the delivery system 10.

Figure 2A:
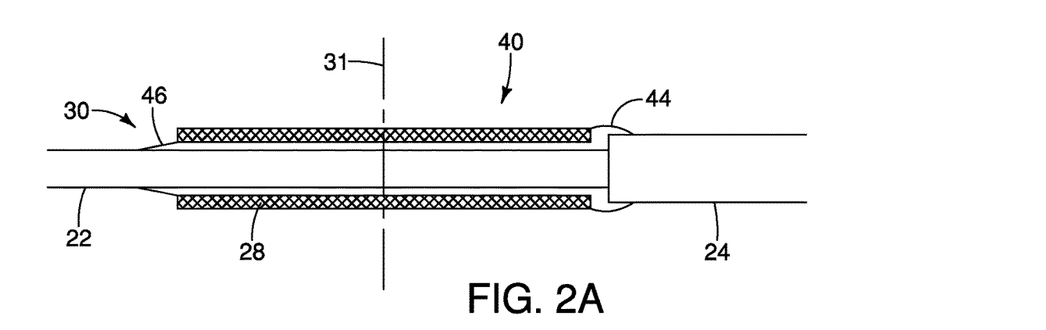
FIG. 2A is a sectional view of a distal portion of the delivery system shown in FIG. 1 showing the stent in a constrained configuration.
Figure 2B:
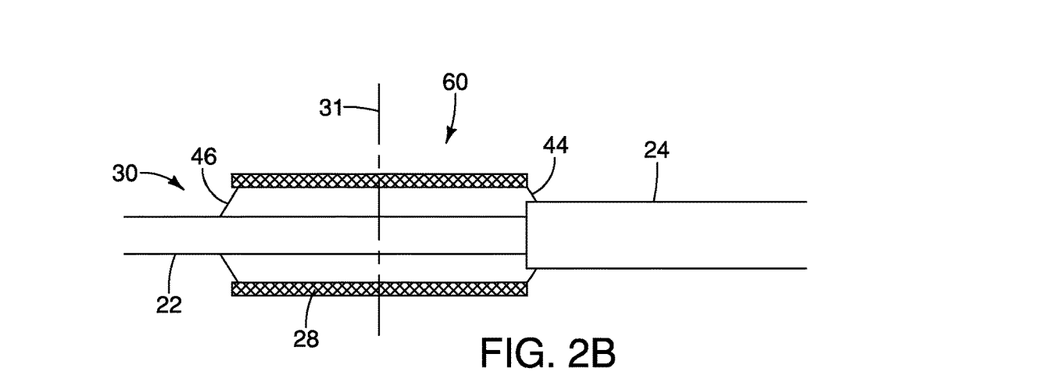
FIG. 2B is a sectional view of a distal portion of the delivery system shown in FIG. 1 showing the stent in an expanded configuration.

FIGS. 2A and 2B illustrate a distal portion 30 of an exemplary stent delivery system 10 that may be driven by a control system in accordance with embodiments of the present invention. The inner shaft 22 and the outer shaft 24 of the stent delivery system 10 are longitudinally movable with respect to each other to facilitate the placement of the stent 28. The stent 28 may be connected to the inner shaft 22 by a distal constraining member 46 and to the outer shaft 24 by a proximal constraining member 44. The stent 28 is movable between a constrained configuration 40 shown in FIG. 2A and an expanded configuration 60 shown in FIG. 2B. As shown in FIG. 2A, the inner shaft 22 is moved distally and the outer shaft 24 is moved proximally to position the stent 28 in the constrained configuration 40. As shown in FIG. 2B, the inner shaft 22 is moved proximally and the outer shaft 24 is moved distally to expand the stent 28 from the constrained configuration 40 to the expanded configuration 60. The embodiment of the distal portion 30 of the delivery system 10 is shown by way of example and meant to be non-limiting. Other configurations for the arrangement of the connection of the stent to the inner and outer shafts for moving the stent between the constrained and expanded configurations are also possible. In some embodiments, one of the inner shaft 22 and the outer shaft 24 may be moved relative to the other of the inner shaft 22 and the outer shaft 24 to move the stent between the constrained configuration 40 and the expanded configuration 60.

Figure 3A:
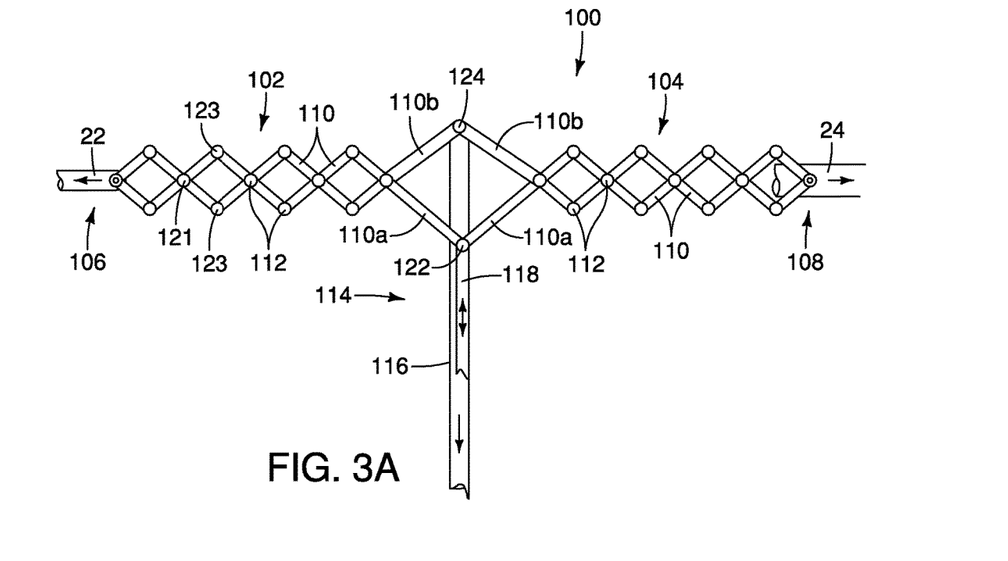
FIG. 3A is a side view of a control mechanism in a first position according to an embodiment of the present invention.
Figure 3B:
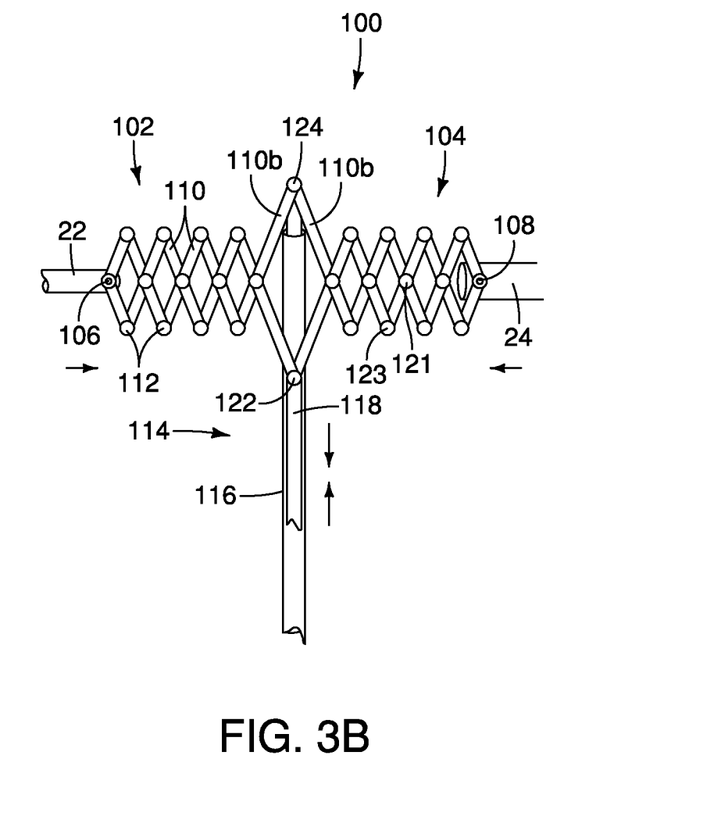
FIG. 3B is a side view of the control mechanism shown in FIG. 3A in a second position.
Figure 5:
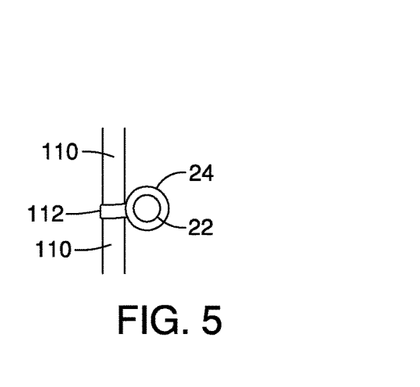
FIG. 5 is a cross-sectional view of a first shaft and a second shaft and a portion of the control mechanism according to an embodiment of the present invention.

An embodiment of a control system 100 is shown FIGS. 3A and 3B. The control system 100 may be provided to facilitate the manipulation of a medical device. The control system 100 may be provided as part of a handle 26 at a proximal portion 27 of the stent delivery system 10 (See FIG. 1). As shown in FIGS. 3A and 3B, the control system 100 includes a first extendable arm 102 operably connected to the inner shaft 22 and a second extendable arm 104 operably connected to the outer shaft 24. As shown in the end view in FIG. 5, the inner and outer shafts 22, 24 may be positioned adjacent the extendable arms 102, 104 and extend coaxially therewith so that the first and second extendable arms 102, 104 may expand and collapse without interference with the longitudinal movement of the inner and outer shafts 22, 24 relative to each other. The first and second extendable arms 102, 104 each include a plurality of crossed struts 110 pivotally connected by a plurality of pins 112 so that the arms 102, 104 are expandable and collapsible to move the stent 28 between the expanded configuration 60 and the constrained configuration 40 as explained in more detail below. The struts 110 are connected at an intermediate point 121 and an end point 123. Depending on the position of the strut 110 in the arm 102, 104, the struts 110 may be connected at two end points 123. The first arm 102 includes a first end 106 and the second arm 104 includes a second end 108.

The first arm 102 and the second arm 104 are operably connected to a control member 114 having a first control pin 116 and a second control pin 118 that are axially movable relative to each other. The first arm 102 and the second arm 104 each include a first strut 110a connected to the first control pin 116 and a second strut 110b connected to the second control pin 118. As shown in FIGS. 3A and 3B, the first and second struts 110a, 110b may be longer than the other struts 110. The longer first and second struts 110a, 110b, may be mechanically advantageous in situations where a longer extension of the ends 106, 108 of the arms 102, 104, respectively, away from each other is desired. The longer first and second struts 110a, 110b provide that a small change in the axial distance between a first attachment point 122 of the first struts 110a and a second attachment point 124 of the second struts 110b causes a larger increase in the distance between the first and second ends 106, 108 of the first and second arms 102, 104 as the attachment points 122, 124 are moved closer together. In some embodiments, all the struts 110 may be the same length, the struts 110 may be different lengths, or the struts 110 on one arm may include longer struts or more struts depending on the amount of longitudinal movement that is desired for the inner and the outer shafts 22, 24 relative to each other. In some embodiments, the length of the first arm 102 is different than the length of the second arm 104 such that the first and second arms travel different distances.

As shown in FIGS. 3A and 3B the control member 114 may be centrally positioned between the first arm 102 and the second arm 104 so that expansion and contraction of the arms 102, 104 is equal and opposite. The first end 106 and the second end 108 are movable in equal and opposite directions to move the inner and outer shafts 22, 24 in equal and opposite directions so that the longitudinal tension on the stent 28 is applied or removed with substantially equal force on both ends of the stent 28. As shown in FIGS. 2A and 2B, when equal and opposite force is applied to and removed from the stent 28, a central portion 31 of the stent 28 remains in the same position as the stent 28 is moved between the constrained configuration 40 and the expanded configuration 68.

Figure 4A:
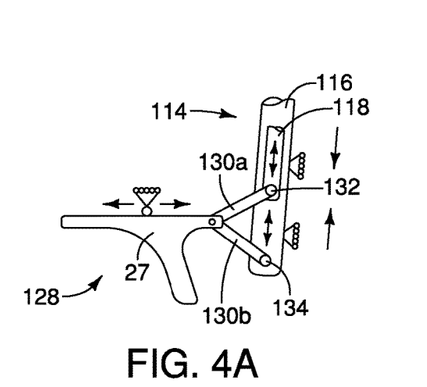
FIG. 4A is a side view of an embodiment of an actuator for a control mechanism according to an embodiment of the present invention.
Figure 4B:
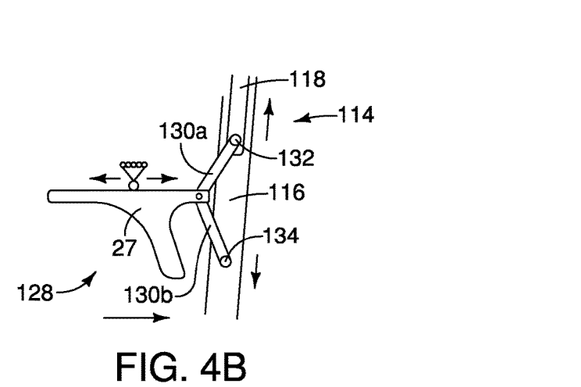
FIG. 4B is a side view of an embodiment of an actuator for a control mechanism according to an embodiment of the present invention in a second position.

FIGS. 4A and 4B illustrate an embodiment of an activator 128 for the control system 100. The activator 128 includes the trigger 27 that is operably connected to the control member 114 via first and second struts 130a and 138b. The first strut 130a is connected to the second control pin 118 at a connection 132 and the second strut 130b is connected to the first control pin 116 at a connection 134. The trigger 27 is longitudinally movable to actuate the axial change in the first and second control pins 116, 118 relative to each other. As the trigger 27 is moved proximally as shown in FIG. 4B, the connections 132, 134 of the first and second struts 130a, 130b are moved apart and the first and second control pins 116, 118 are moved in opposite directions. The attachment points 122, 124 (shown in FIG. 3A) are moved closer together and the ends 106, 188 of the arms 102, 104 extend away from each other to move the stent to the constrained configuration 40 shown in FIG. 2A. The trigger 27 may be returned to the starting position by any means known in the art. Non-limiting examples include spring return or manual return.

The control system 108 shown in FIG. 3B illustrates the system 100 position when the stent 28 is in the expanded configuration 60 shown in FIG. 2B. The ends 106, 188 of the arms 102, 104 are positioned closer together and the inner shaft 22 is moved proximally and the outer shaft 24 is moved distally releasing the longitudinal tension on the stent 28. As shown in FIG. 3B, the attachment points 122, 124 are moved farther apart so that the arms 102, 104 fold inward as the struts 110 pivot on the pins 112. The corresponding position of the actuator 128 is shown in FIG. 4A where the connections 132, 134 are positioned closer together relative to the position of the connections 132, 134 shown in FIG. 4B.

As shown in FIGS. 2A, 3A and 4A, the stent 28 is moved to the constrained configuration 40 by pulling the trigger 27 of the actuator 128 proximally. As will be understood by one skilled in the art, the control system 100 may be provided so that pulling the trigger 27 of the actuator 128 proximally expands the stent 28, to the expanded configuration 60. By way of non-limiting example, the struts 110a may be connected to the second pin 118 and the struts 110b may be connected to the first pin 116 so that moving the trigger 27 proximally moves the attachment points 122, 124 away from each other and the stent 28 moves to the expanded configuration 60. The control system 100 may include a lock to lock the stent 28 in the constrained configuration 40, for example during delivery to the treatment site or in the expanded configuration 60.

Figure 6:
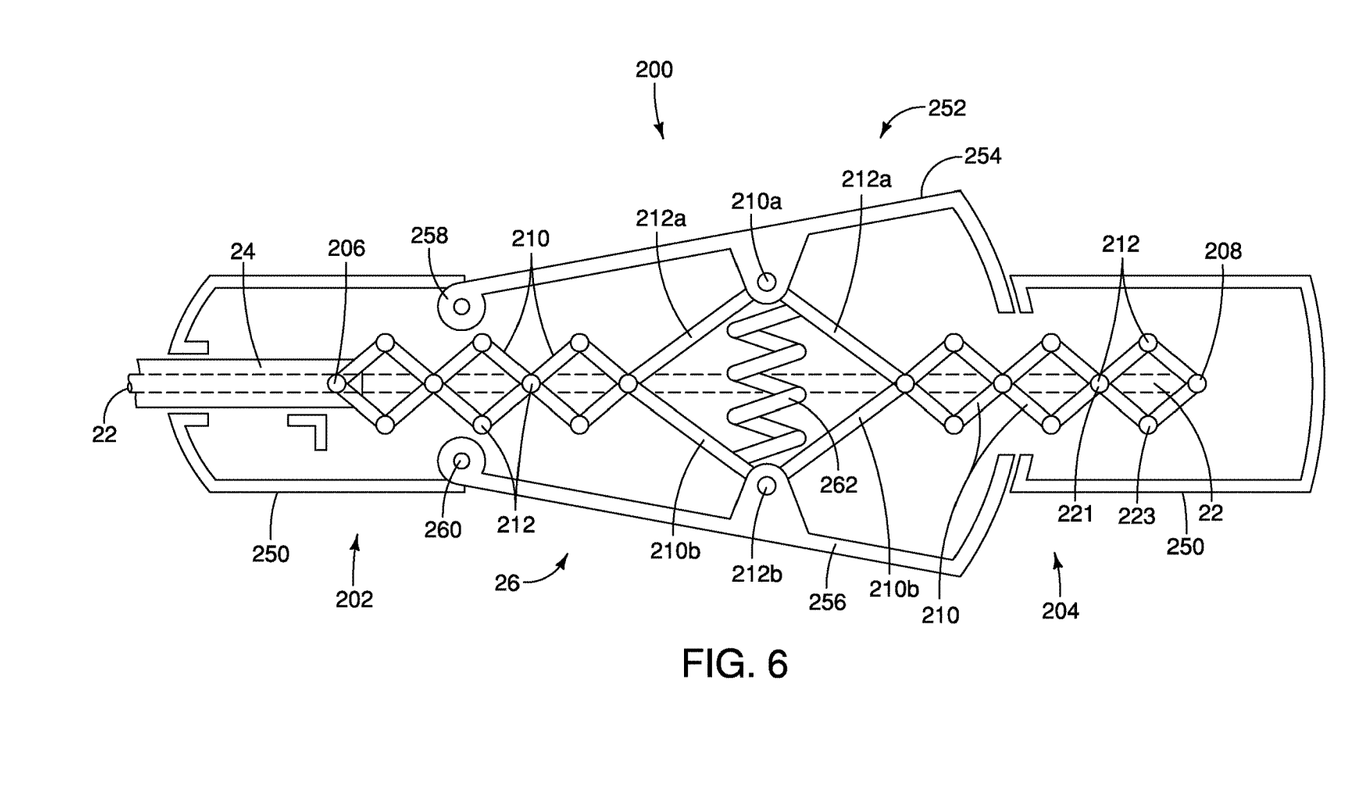
FIG. 6 is a side view of an alternative embodiment of a control mechanism.

Another embodiment of a control system 200 is shown in FIG. 6. The control system 200 may be provided as part of a handle 26 of the stent delivery system 10. As shown in FIG. 6, the control system 200 may be provided with a housing 250 and includes a first extendable arm 202 operably connected to the outer shaft 24 and a second extendable arm 204 operably connected to the inner shaft 22. The first and second extendable arms 202, 204 each include a plurality of crossed struts 210 pivotally connected by a plurality of pins 212 so that the arms 202, 204 are expandable and collapsible to move the stent 28 between the expanded configuration 60 and the constrained configuration 40. The struts 210 are connected at an intermediate point 221 and an end point 223. Depending on the position of the strut 210 in the arm 202, 204, the struts 210 may be connected at two end points 223. The first arm 202 includes a first end 206 and the second arm 204 includes a second end 208.

The housing 250 may further include an actuator 252 having a first actuator arm 254 and a second actuator arm 256 that cooperate to longitudinally move the inner and outer shafts 22, 24 relative to each other to expand and collapse the stent 28. The first and second actuator arms 254, 256 move on pivots 258, 260. The first arm 202 and the second arm 204 are operably connected to the actuator 252 so that the movement of the actuator 252 moves the arms 202, 204 that move the inner and outer shafts 22, 24. The housing 250 may further include a biasing member 262 positioned between the first and second actuator arms 254, 256 to return the first and second actuator arms 254, 256 to a starting position.

The first arm 202 and the second arm 204 each include a first strut 210a connected to the first actuator arm 254 by a pin 212a. The first arm 202 and the second arm 204 also each include a second strut 210b connected to the second actuator arm 256 by a pin 212b. As shown in FIG. 6, the first and second struts 210a, 210b may be longer than the other struts 210 of the first and second arms 202, 204 similar to the first and second struts 110a, 110b described above. In some embodiments, all the struts 210 may be the same length, the struts may be different lengths, or the struts on one arm may include longer struts or more struts depending on the amount of longitudinal movement that is desired for the inner and the outer shafts 22, 24 relative to each other.

The first arm 202 and the second arm 204 may be the same length or different lengths depending on how far the inner and outer shafts 22, 24 are to be longitudinally moved relative to each other. In some embodiments, the first and second extendable arms 202, 204 are equal in length so that expansion and contraction of the arms 202, 204 is equal and opposite. The first end 206 and the second end 208 are movable in opposite directions to move the inner and outer shafts 22, 24 in opposite directions so that the longitudinal tension is applied to or removed from the stent 28. For embodiments having arms 202, 204 with equal length, the longitudinal tension is applied with equal and opposite force. As shown in FIGS. 2A and 2B, when equal and opposite force is applied to and removed from the stent 28, a central portion 31 of the stent 28 remains in the same position as the stent 28 is moved between the constrained configuration 40 and the expanded configuration 60.

As shown in FIG. 6, when the actuator arms 254, 256 are pressed axially inward toward each other, the ends 206, 208 of the arms 202, 204 move longitudinally away from each other and extend. The inner shaft 22 is moved proximally and the outer shaft 24 is moved distally and longitudinal tension is removed from the stent 28 to move the stent 28 to the expanded configuration 60. In an alternative embodiment, the outer shaft 24 may be connected to the second extendable arm 204 and the inner shaft 22 connected to the first extendable arm 202 so that the stent 28 is moved to the constrained configuration 40. In the alternative embodiment, pressing on the actuator arms 254, 256 moves the ends 206, 208 of the arms 202, 204 away from each other and extend the arms 202, 204. The outer shaft 24 is moved distally and the inner shaft 22 is moved proximally and longitudinal tension is applied to the stent 28 to move the stent 28 to the constrained configuration 40.

Figure 7:
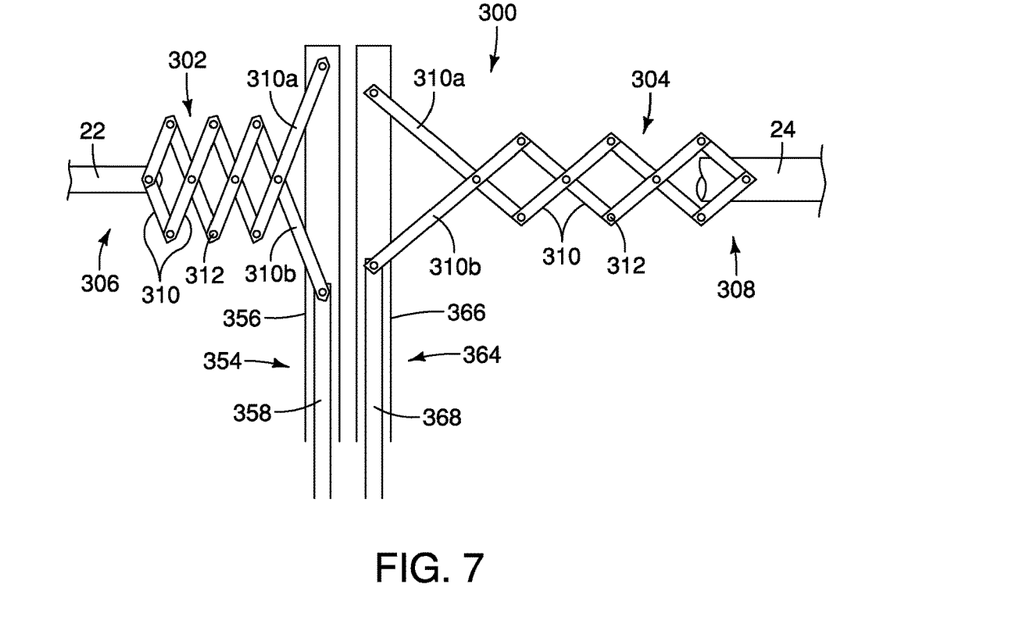
FIG. 7 is a side view of an alternative embodiment of a control mechanism.

Another embodiment of a control system 300 is shown in FIG. 7. The control system 300 may be provided as part of a handle 26 at a proximal portion 27 of the stent delivery system 10 (See FIG. 1). As shown in FIG. 7, the control system 300 includes a first extendable arm 302 operably connected to the inner shaft 22 and a second extendable arm 304 operably connected to the outer shaft 24. In some embodiments, the outer shaft 24 may be connected to the first extendable arm 302 and the inner shaft 22 may be connected to the second extensible arm 304. The first and second extendable arms 302, 304 each include a plurality of crossed struts 310 pivotally connected by a plurality of pins 312 so that the arms 302, 304 are expandable and collapsible to move the stent 28 between the expanded configuration 60 and the constrained configuration 40 as explained above. The first arm 302 and the second arm 304 may be extendable to the same length or to different lengths. The first arm 302 includes a first end 306 and the second arm 304 includes a second end 308.

The first arm 302 is operably connected to a control member 354 having a first control pin 356 and a second control pin 358 that are axially movable relative to each other. The first arm 302 includes a first strut 310a connected to the first control pin 356 and a second strut 310b connected to the second control pin 358. The second arm 304 is operably connected to a control member 364 having a first control pin 366 and a second control pin 368 that are axially movable relative to each other. The second arm 304 includes a first strut 310a connected to the first control pin 366 and a second strut 310b connected to the second control phi 368. As shown in FIG. 7, the first and second struts 310a, 310b may be the same length as the other struts 310. In some embodiments, the struts 310 may be different lengths, or the struts 310 on one arm may include longer struts or more struts depending on the amount of longitudinal movement that is desired for the inner and the outer shafts 22, 24 relative to each other. Similar to the embodiments described above, the first and second struts 310a and 310b may be longer than the rest of the struts 310 to provide greater longitudinal extension of the arms 302, 304 with relatively small axial movement.

As shown in FIG. 7, the first and second arms 302, 304 may be controlled separately by control members 354, 364 respectively so that one arm or both arms may be extended and contracted to apply and remove longitudinal tension on the stent 28. As shown in FIG. 7, the first arm 302 is contracted and the second arm 304 is expanded. The first end 306 and the second end 308 are movable in opposite directions and the first arm 302, the second arm 304 or both may be activated to move the inner shaft 22, the outer shaft 24 or both the inner and outer shafts 22, 24 relative to each other. In some embodiments, the control members 354, 364 may be operated together so that expansion and contraction of the arms 302, 304 occurs at the same time. In some embodiments where the control members 354, 364 are operated together, expansion and contraction of the arms 302, 304 is in equal and opposite directions so that the longitudinal tension on the stent 28 is substantially equal and opposite and the central portion 31 of the stent 28 remains in the same position as the stent 28 is moved between the constrained and expanded configurations 40, 60. (See FIGS. 2A and 2B.)

Figure 8:
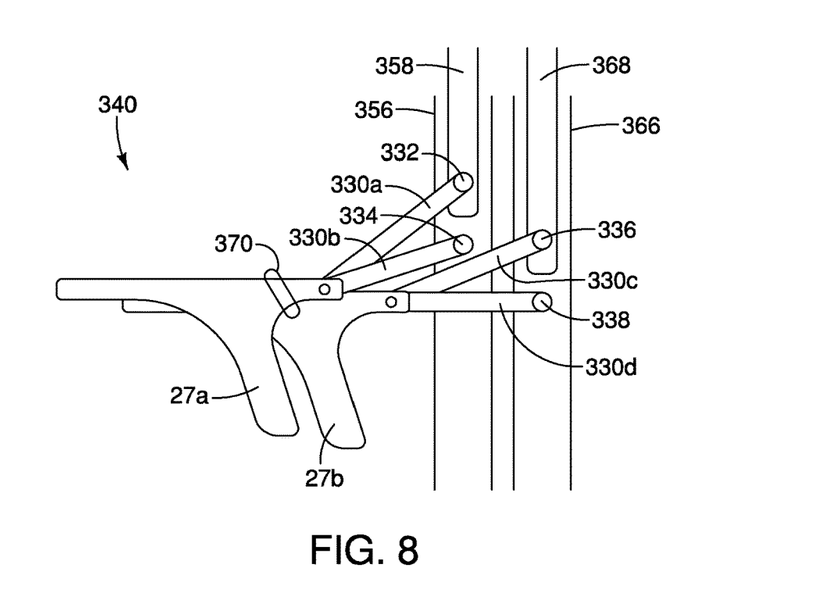
FIG. 8 is a side view of an actuator for an embodiment of the control mechanism.

FIG. 8 illustrates an embodiment of an activator 340 for the control system 300. The activator 340 may include a first trigger 27a and a second trigger 27b. The first trigger 27a is operably connected to the control member 354 via first and second struts 330a, 330b and the second trigger 27b is operably connected to the control member 364 via first and second struts 330c, 330d. The first strut 130a is connected to the first trigger 27a and to the second control pin 358 at a connection 332. The second strut 130b is connected to the first trigger 27a and the first control pin 356 at a connection 334. The first strut 330c is connected to the second trigger 27b and to the second control phi 368 at a connection 336. The second strut 130d is connected to the second trigger 27b and the first control pin 366 at a connection 338. The triggers 27a and 27b are longitudinally movable to actuate the axial change in the first and second control pins 356, 358 of the control member 354 relative to each other and the first and second control pins 366, 368 of the control member 364 relative to each other. As the trigger 27a is moved proximally, the control member 354 is activated and the first arm 302 is extended. As the trigger 27b is moved proximally, the control member 364 is activated and the second arm 304 is extended. As shown, the ends 306, 308 of the arms 302, 304 extend in opposite directions. The triggers 27a and 27b may be releasably locked together with a connector 370 to cooperatively control activation of the control members 354, 364 to cooperatively extend and contract the first and second arms 302, 304. The triggers 27a and 27b may be returned to the starting position by any means known in the art. Non-limiting examples include spring return or manual return.

Figure 9:
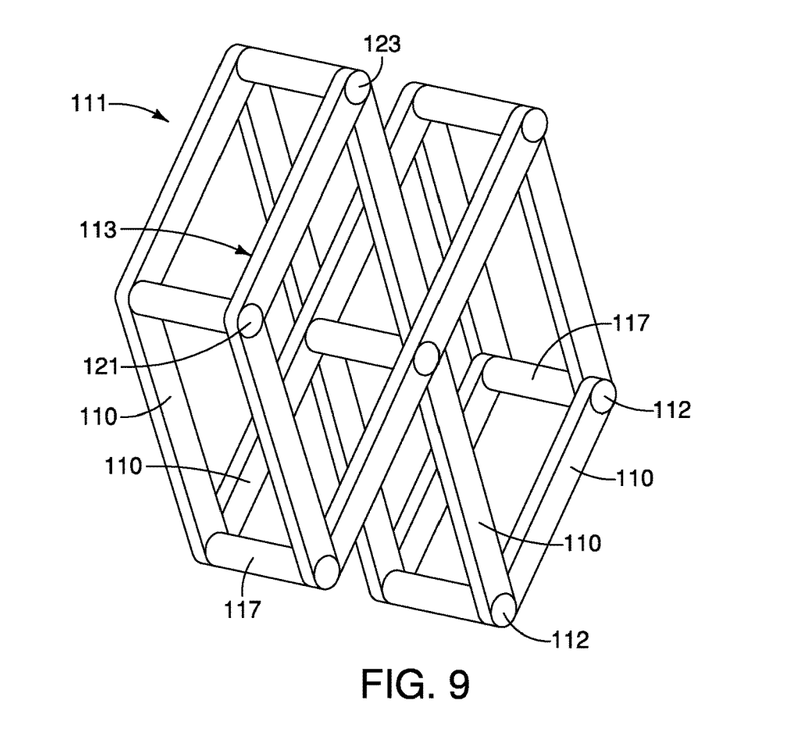
FIG. 9 is an enlarged perspective view of a portion of an array of an embodiment of the control mechanism.

In some embodiments, the arms of the control mechanism may be provided in a double strut configuration for additional stability. For example, arms 102 and 104 may be provided with pairs of struts 110 as shown in FIG. 9. The pairs of struts 110 include a first set 111 and a second set 113 that are substantially parallel to each other and extendable together. The struts 110 may be connected by pins 112 as described above and further include connectors 117 extending between the first set 111 and the second set 113. Alternatively, the connectors 117 may be provided to connect the first set 111 to the second set 113 and also to provide pivot points for the struts 110 connected to each other. The pairs of struts 110 may be included with any of the embodiments described above to provide additional stability.

Figure 10:
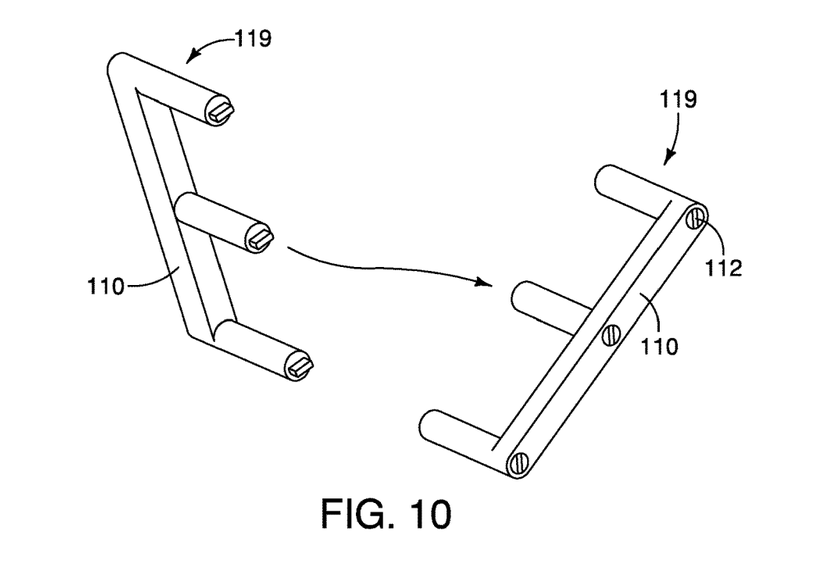
FIG. 10 is an enlarged perspective view of a portion of an arm of an embodiment of the control mechanism.

In some embodiments, the struts 110 may be provided as molded components that can be locked together by snap fit or tab and slot arrangements so that fewer parts are needed to assembly the arms of the control mechanism. Exemplary molded components 119 are shown in FIG. 10. Any form of struts may be used to form the arms of the control member. Molded components are but one example of many types of struts that may be used.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A control system for controlling movement of a medical device delivery system having a first shaft and a second shaft, the first shaft movable relative to the second shaft, the control system comprising:
   a first arm comprising a first end portion, the first arm movable between a first position and a second position; the first arm operably connectable to one of the first shaft and the second shaft;
   a second arm comprising a second end portion, the second arm operably connectable to the other of the first shaft and the second shaft;
   a first actuator operably connected to the first arm; the first actuator operable to move the first arm from the first position to the second position; and
   a biasing member for biasing the first actuator, wherein the biasing member is positioned between the first arm and the second arm;
   wherein movement of the first arm moves the first shaft relative to the second shaft to change the position of the second shaft relative to the first shaft
   wherein the first actuator comprises a first actuator member and a second actuator member; and
   wherein the biasing member biases the first actuator member and the second actuator member away from each other.

2. The control system of claim 1, wherein the first arm comprises a plurality of struts interconnected at intermediate points and end points of the struts of the first arm.

3. The control system of claim 2, wherein the second arm comprises a plurality of struts interconnected at intermediate points and end points of the struts of the second arm.

4. The control system of claim 3, wherein the plurality of struts of the first arm and the plurality of struts of the second arm are formed from molded components.

5. The control system of claim 2, wherein the plurality of struts of the first arm comprises a first actuator strut connected to the first actuator, the first actuator strut having a length greater than the other struts of the first arm.

6. The control system of claim 1, wherein the first arm is movable in a first direction and the second arm is movable in an opposite direction to the first direction.

7. The control system according to claim 1, wherein the biasing member is positioned between the first actuator member and the second actuator member.

8. A stent delivery system comprising:
   a first shaft;
   a second shaft, the second shaft movable relative to the first shaft and coaxially extending with the first shaft;
   a stent operably connected to the first shaft and the second shaft, the stent having a constrained configuration and an expanded configuration; and
   a control system comprising:
      a first arm, the first arm movable between a first position and a second position; the first arm operably connected to one of the first shaft and the second shaft;
      a second arm operably connected to the other of the first shaft and the second shaft; and
      a first actuator operably connected to the first arm, the first actuator being pivotally connected to an end of the first arm and to an end of the second arm; the first actuator operable to move the first arm from the first position to the second position, the first actuator comprising a first actuator member and a second actuator member;
   wherein movement of the first arm moves the first shaft relative to the second shaft to move the stent to the constrained configuration or the expanded configuration
   wherein the first arm comprises a plurality of struts interconnected at intermediate points and end points of the struts of the first arm and the second arm comprises a plurality of struts interconnected at intermediate points and end points of the struts of the second arm.

9. The delivery system of claim 8, wherein the control system further comprises a biasing member for biasing the first actuator.

10. The delivery system of claim 9, wherein the biasing member biases the first actuator member away from the second actuator member.

11. The delivery system of claim 9, wherein the biasing member biases the first actuator so that the stent is in the constrained configuration.

12. The delivery system of claim 8, wherein the first actuator member is operably connected to one strut of the first arm and one strut of the second arm and the second actuator member is operably connected to another strut of the first arm and another strut of the second arm.

13. The stent delivery system according to claim 8, wherein the first actuator is directly pivotally connected to the first arm and the second arm or the first actuator is indirectly pivotally connected to the end of the first arm and the second arm via a control member.

14. A method of controlling the movement of a medical device delivery system, the method comprising:
   providing a control system, the control system comprising:
      a first arm comprising a plurality of struts interconnected at intermediate points and end points of the struts of the first arm, the first arm movable between a first position and a second position; the first arm operably connected to one of a first shaft and a second shaft of the medical device delivery system;

a second arm comprising a plurality of struts interconnected at intermediate points and end points of the struts of the second arm, the second arm operably connected to the other of the first shaft or the second shaft; and a first actuator operably connected to the first arm, the first actuator being pivotally connected to an end of the first arm and to an end of the second arm; the first actuator operable to move the first arm from the first position to the second position, the first actuator comprising a first actuator member and a second actuator member wherein the first arm comprises a plurality of struts interconnected at intermediate points and end points of the struts of the first arm and the second arm comprises a plurality of struts interconnected at intermediate points and end points of the struts of the second arm;

activating the first actuator by moving the first actuator member relative to the second actuator member;

moving the first arm in response to the activation of the first actuator; and changing the position of the first shaft relative to the second shaft.

15. The method of claim 14, further wherein moving the first arm changes a configuration of a stent to an expanded configuration or a constrained configuration.

16. The method of claim 14, further comprising biasing the first actuator with a biasing member.

17. The method of claim 14, further comprising changing a longitudinal tension on a stent operably connected to the first shaft and the second shaft by changing the position of the first shaft relative to the second shaft.

* * * * *